United States Patent
Awoniyi

(10) Patent No.: US 6,666,211 B1
(45) Date of Patent: Dec. 23, 2003

(54) NOSE BLEED TREATMENT DEVICE

(76) Inventor: Wilnelsia A. Awoniyi, 826 NW. 90th Ter., Plantation, FL (US) 33324

(*) Notice: Subject to any disclaimer, the term of this patent is extended or adjusted under 35 U.S.C. 154(b) by 0 days.

(21) Appl. No.: 10/382,206

(22) Filed: Mar. 5, 2003

Related U.S. Application Data

(60) Provisional application No. 60/361,933, filed on Mar. 6, 2002.

(51) Int. Cl.$^7$ .................................................. A61F 4/00
(52) U.S. Cl. ...................................... 128/858; 606/196
(58) Field of Search .............................. 128/846, 848, 128/857, 858; 606/196, 197

(56) References Cited

U.S. PATENT DOCUMENTS

| | | | | |
|---|---|---|---|---|
| 2,215,126 A | * | 9/1940 | McMillin | 606/196 |
| 3,570,494 A | * | 3/1971 | Gottschalk | 606/196 |
| 3,935,859 A | * | 2/1976 | Doyle | 606/196 |
| 4,338,941 A | * | 7/1982 | Payton | 128/325 |
| 4,534,342 A | * | 8/1985 | Paxe | 128/163 |
| 5,383,891 A | * | 1/1995 | Walker | 606/196 |

* cited by examiner

Primary Examiner—Michael A. Brown
(74) Attorney, Agent, or Firm—Joseph N. Breaux

(57) ABSTRACT

A nose bleed treatment device that includes a molded adhesive coated foam shell shaped to conform to the nose of a patient as well as a pair of tubular, open-cell foam nostril insert assemblies. The inner surface of the shell adjacent the nose is coated with a synthetic acrylic latex adhesive for temporary adhesion to the nose during use and has a peel-off cover positioned on the latex adhesive covered area during assembly. The nostril inserts are each formed from a hypoallergenic material and have a semi-rigid tube maintaining an air passage there through in an open condition even when swollen with fluid during use.

1 Claim, 2 Drawing Sheets

NOSE BLEED TREATMENT DEVICE

This Application claims the benefit of Provisional Application Ser. No. 60/361,933 filed Mar. 6, 2002.

TECHNICAL FIELD

The present invention relates to medical bandages and more articularly to a nose bleed treatment device that includes a molded adhesive coated foam shell shaped to conform to the nose of a patient; an inner surface adjacent the nose is coated with a synthetic acrylic latex adhesive for temporary adhesion to the nose during use; a peel-off cover positioned on the latex adhesive covered area; and a pair of tubular, open-celled foam cylinders sized and shaped to fit into a nostril of a patient and formed from a hypo-allergenic polyurethane polymer are attached to the interior surface of the shell; a semi-rigid tube formed of low density polyethylene is positioned within each of the tubular, open-celled foam cylinders to maintain an air flow passage through each cylinder; the outer layer of the device being covered with a cotton gauze.

BACKGROUND ART

Many individuals suffer from nose bleeds. It would be desirable, therefore, to have a treatment device that could be rapidly applied during a nose bleed that would aid in reducing the length of the nose bleed, as well as, the amount of blood lost and would capture the blood for disposal.

GENERAL SUMMARY DISCUSSION OF INVENTION

It is thus an object of the invention to provide a nose bleed treatment device that includes a molded adhesive coated foam shell shaped to conform to the nose of a patient; an inner surface adjacent the nose is coated with a synthetic acrylic latex adhesive for temporary adhesion to the nose during use; a peel-off cover positioned on the latex adhesive covered area; and a pair of tubular, open-celled foam cylinders sized and shaped to fit into a nostril of a patient and formed from a hypo-allergenic polyurethane polymer are attached to the interior surface of the shell; a semi-rigid tube formed of low density polyethylene is positioned within each of the tubular, open-celled foam cylinders to maintain an air flow passage through each cylinder; the outer layer of the device being covered with a cotton gauze.

Accordingly, a nose bleed treatment device is provided. The nose bleed treatment device includes a molded adhesive coated foam shell shaped to conform to the nose of a patient; an inner surface adjacent the nose is coated with a synthetic acrylic latex adhesive for temporary adhesion to the nose during use; a peel-off cover positioned on the latex adhesive covered area; and a pair of tubular, open-celled foam cylinders sized and shaped to fit into a nostril of a patient and formed from a hypo-allergenic polyurethane polymer are attached to the interior surface of the shell; a semi-rigid tube formed of low density polyethylene is positioned within each of the tubular, open-celled foam cylinders to maintain an air flow passage through each cylinder; the outer layer of the device being covered with a cotton gauze.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
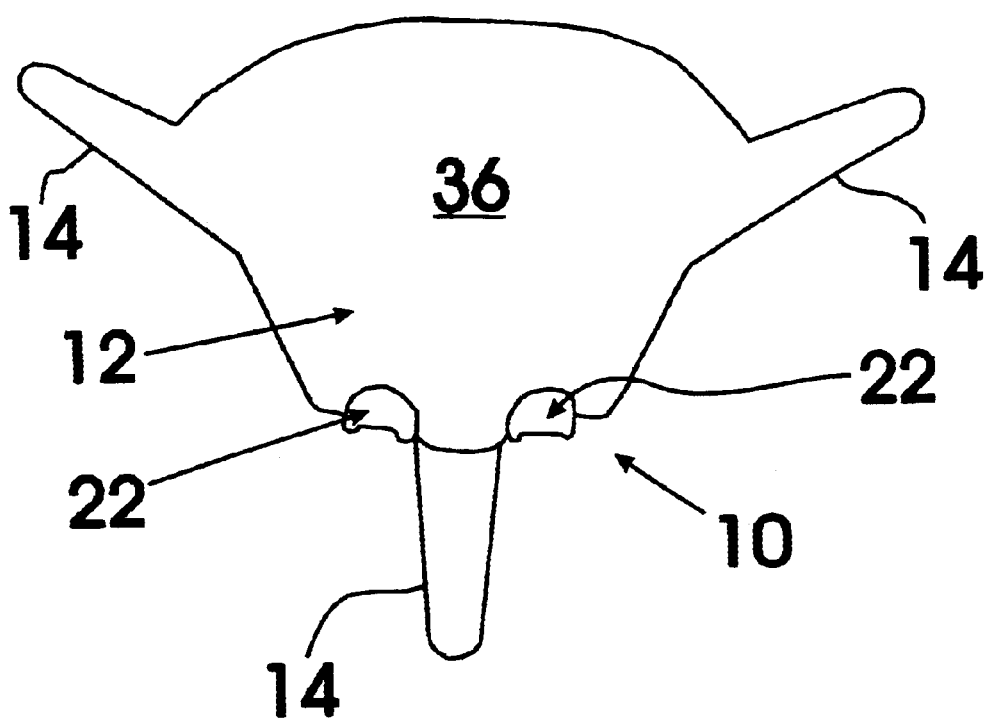
FIG. 1 is a front view of an exemplary embodiment of the nose bleed treatment device of the present invention.
Figure 2:
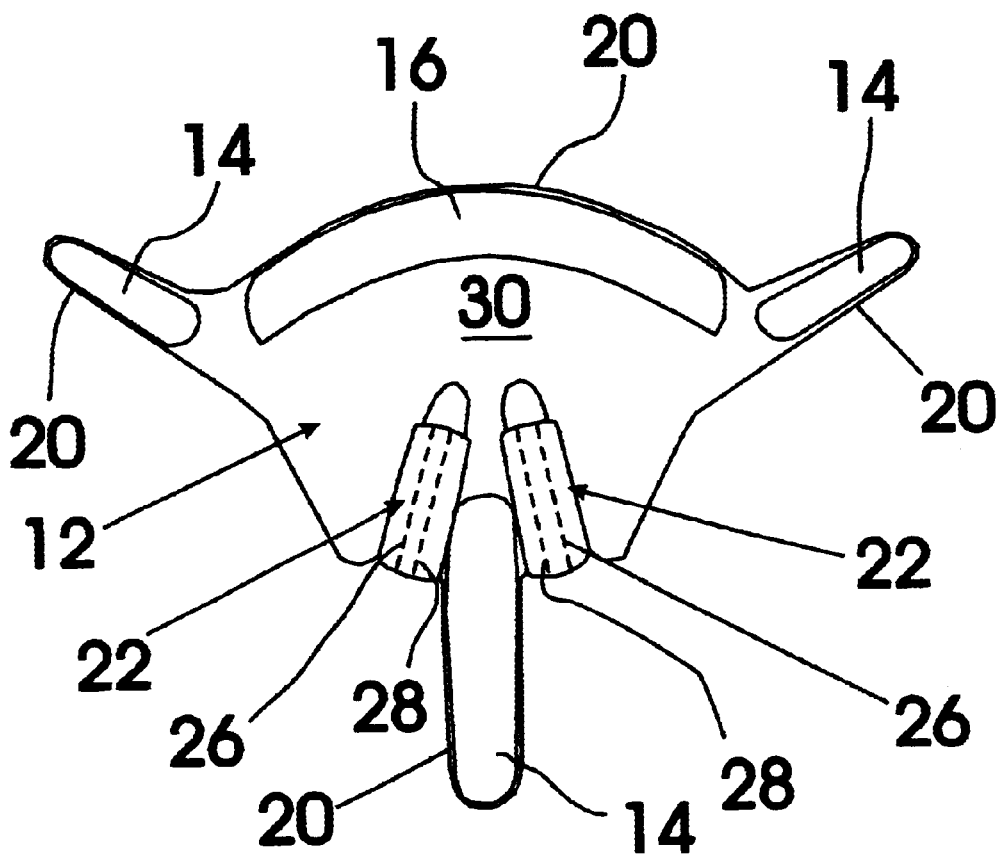
FIG. 2 is a rear end view of the nose bleed treatment device of FIG. 1.

FIGS. 1–2 show various aspects of an exemplary embodiment of the nose bleed treatment device of the present invention generally designated 10. Nose bleed treatment device 10 includes a molded adhesive coated foam shell, generally designated 12, shaped to conform to the nose of a patient and provided with three adhesive strips 14. In addition, an inner surface 16 adjacent the nose is coated with a synthetic acrylic latex adhesive for temporary adhesion to the nose during use. A peel-off cover 20 is positioned on the latex adhesive covered area 16 as well as the adhesive strips 14.

Device 10 also includes two tubular, open-celled foam cylinders, generally designated 22, sized and shaped to fit into a nostril of a patient and having a air passageway 26 that is kept open by a semi-rigid tube 28 that is formed of low density polyethylene. Each of the two open-celled foam cylinders 22 is formed from a hypo-allergenic polyurethane polymer and is attached to the interior surface 30 of shell 12.

The outer layer 36 of device 10 is covered with a cotton gauze that may be colored or dyed any desirable color.

It can be seen from the preceding description that a nose bleed treatment device has been provided.

It is noted that the embodiment of the nose bleed treatment device described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A nose bleed treatment device comprising:
    a molded adhesive coated foam shell shaped to conform to the nose of a patient;
    an inner surface of the foam shell to be worn adjacent the nose is coated with a synthetic acrylic latex adhesive for temporary adhesion to the nose during use;
    a peel-off cover is positioned on the latex adhesive covered area for storage; and
    a pair of tubular, open-celled foam cylinders sized and shaped to fit into the nostrils of a patient and formed from a hypo-allergenic polyurethane polymer are attached to the interior surface of the shell;
    a semi-rigid tube formed of low density polyethylene is positioned within each of the tubular, open-celled foam cylinders to maintain an air flow passage through each cylinder;
    an outer layer of the device being covered with a cotton gauze.

* * * * *